United States Patent [19]

Dolan

[11] Patent Number: 4,911,694
[45] Date of Patent: Mar. 27, 1990

[54] SYRINGE NEEDLE SHEATH

[76] Inventor: Michael F. Dolan, 112 Mt. Pleasant Ave., West Orange, N.J. 07052

[21] Appl. No.: 191,153

[22] Filed: May 6, 1988

[51] Int. Cl.[4] .............................................. A61M 5/32
[52] U.S. Cl. .................................... 604/198; 604/171; 604/164; 604/110
[58] Field of Search ............... 604/171, 164, 198, 197, 604/192, 110, 263, 443

[56] References Cited

U.S. PATENT DOCUMENTS

| | | |
|---|---|---|
| 2,711,732 | 6/1955 | Solomon . |
| 2,847,995 | 8/1958 | Adams . |
| 3,134,380 | 5/1964 | Armao . |
| 3,662,754 | 5/1972 | Halloran . |
| 4,026,287 | 5/1964 | Haller . |
| 4,139,009 | 2/1979 | Alvarez . |
| 4,273,123 | 1/1981 | Lemelson . |
| 4,592,744 | 6/1986 | Jagger et al. . |
| 4,623,336 | 11/1986 | Pedicano et al. . |
| 4,634,428 | 1/1987 | Cuu . |
| 4,650,468 | 3/1987 | Jennings, Jr. . |
| 4,654,034 | 3/1987 | Masters et al. . |
| 4,675,005 | 6/1987 | DeLuccia . |
| 4,676,783 | 6/1987 | Jagger et al. . |
| 4,713,057 | 12/1987 | Huttner et al. ...................... 604/164 |
| 4,790,828 | 12/1988 | Dombrowski et al. .............. 604/198 |

Primary Examiner—Stephen C. Pellegrino
Attorney, Agent, or Firm—Cushman, Darby and Cushman

[57] ABSTRACT

A syringe needle assembly including a needle having at least one point for use in a syringe assembly, including a needle shaft with at least one point at one end for entering the patient and one end for engaging the syringe, and a puncture-proof sheath surrounding a major portion of the needle shaft and normally extending substantially the entire length of the shaft while leaving said needle point exposed, the sheath including at least one radially expanded inner portion joined by a portion attached to said shaft, the radially expanded portion being axially compressible to force the sheath to slide in the direction of said point along said shaft to extend beyond and non-retractably cover said point. The present invention is specifically adapted to sheath a single pointed or double pointed needle.

29 Claims, 4 Drawing Sheets

SYRINGE NEEDLE SHEATH

BACKGROUND AND SUMMARY OF THE INVENTION

The present invention relates to syringe assemblies, and more specifically relates to a syringe needle assembly which includes a permanently attached and extendable sheath which covers the point(s) of the needle after use.

In recent years, there has been an urgent need to protect medical practitioners from possible infection by exposure to used syringe needles. Such syringe needles may have been employed for phlebotomy, hypodermic injections, biopsies, intravenous feeding, and other uses where a needle has entered the patient's body. The concern for contacting serum hepatitis and acquired immune deficiency syndrome (AIDS) is particularly acute.

When a syringe needle is to be sterilized and reused, the medical practitioner is exposed from the time of completing the medical procedure to the time of sterilizing the syringe apparatus. When the syringe needle assembly is to be disposed, then not only is the medical practitioner exposed to possible infection, but anyone coming into contact with the refuse is also potentially at risk of infection.

While medical practitioners may take such prophylactic measures as wearing gloves, needle pricks are still possible. In phlebotomy, for example, medical personnel may experience one prick out of 100 blood draws. When a needle has two points, such as in the use of Vacutainer syringes, the probability of becoming pricked is even greater.

To date, while various protective measures have been proposed, few have gained widespread acceptance in the medical community. Not only has the complexity and relative high cost of prior assemblies deterred their common employment, but even more important today, they do not adequately protect the medical practitioner from possible infection. Furthermore, while there have been prior attempts to adequately cover syringe needles for protective purposes, all known attempts have been directed to single point needles, with no known assembly to cover the points of a double pointed needle.

In view of the foregoing, an object of the present invention is to provide a syringe assembly including a puncture-proof sheath which may be extended in both directions along the shaft of a double pointed needle to non-retractably cover the points of the needle after use.

It is an object of the invention to provide a syringe needle having a protective sheath which may be operated by medical practitioners using the finger-tips of one hand to actuate the protective device without having to touch the used needle with the exposed fingertips.

It is a further object of the invention to form in combination with the outlet of a a syringe, a locking assembly so that the needle cannot be removed from the syringe until the protective sheath has been employed to cover the needle points.

It is a still further object of the present invention to provide a syringe assembly including a puncture-proof sheath extendable to non-retractably cover the single point of a syringe needle, being extended by the fingertips of one hand as in covering a double pointed needle.

SUMMARY OF THE INVENTION

In accordance with a presently preferred exemplary embodiment, the foregoing objects and others are achieved in a syringe assembly including a permanently attached and extendable puncture-proof sheath for covering the shaft and point(s) of the needle.

The present syringe needle sheath is a protective device disclosed in three embodiments: the first and third for protecting both points of a double pointed (e.g. Vacutainer) syringe needle, and the second for protecting the point of a common single pointed needle. The protective sheath is to be permanently attached to the needle but only actuated to cover and protect the point(s) of the needle after the needle has been used. Once employed, the protective sheath prevents accidental post-use stabbing (sticks) of medical practitioners handling the possibly contaminated needle. The used needle may be safely discarded with little risk of contaminating medical practitioners or others coming into contact with the needle.

The syringe assembly may be used with conventional syringes such as those of a reusable or disposable type. The syringe assembly includes a needle having one or two points, one point for entering the patient and one point for entering the syringe, or flat end for interfacing with the syringe. The assembly includes a puncture-proof sheath surrounding the needle and substantially extending the length of the needle shaft, one or both of the needle points being exposed, the sheath including at least one radially expanded portion of the sheath which when compressed, forces an end of the sheath to slide in a direction along the shaft to extend beyond and cover the point. At least two radially expanded portions would be employed to cover both points of a double-pointed needle. The syringe assembly may further include a hub portion adapted for attachment to the outlet end of a syringe. The hub, in the first embodiment, has a medial passageway containing a portion of the needle shaft and sheath. In the second embodiment, for a single pointed needle, the hub only contains the shaft. In the third embodiment (double pointed needle), the hub only contains the shaft and further holds an arm of the sheath at the hub exterior which engages pawls in the outlet of the syringe, thus locking the needle to the syringe until the protective sheath has been employed to cover the needle points. The hub generally enables tight securement of the needle to the syringe for liquid flow to or from the outlet of the syringe. An annular collar is an integral portion of the hub for positioning the hub in relation to the syringe outlet.

A compression platform member may further be provided which enables greater fingertip control in compressing the radially expanded portion(s) of the sheath. The compression platform may include a locking member which facilitates the non-retractable nature of the sheath once extended to cover the point(s). A locking device, such as a friction clamp, may also be employed on the inner surface of the expanded portion of the sheath.

In operation, after using the syringe needle, a medical practitioner would compress the radially expanded portion of the sheath with fingertips, thus forcing the sheath to slide along the shaft of the needle to cover the point(s). If a locking device or compression platform with a locking device is employed, then the fingertip compression of the radially expanded portion of the sheath would force the locking device towards the needle shaft, flattening the radially expanded portion, so that the locking device engages, for example, the needle shaft, to more securely prevent retraction of the sheath.

Advantages of the presently claimed invention include: (1) a puncture resistant or puncture-proof sheath; (2) a non-retractable sheath covering the exposed needle tips after use; (3) a locking mechanism between the needle and syringe; and (4) the protective sheath being designed to allow essentially single-handed implementation of the device without having to touch the used needle at all.

BRIEF DESCRIPTION OF THE DRAWINGS

Further objects and advantages of the present invention will be better understood by carefully reading the following detailed description of the presently preferred exemplary embodiments of this invention in conjunction with the accompanying drawings of which.

DETAILED DESCRIPTION OF THE PREFERRED EMBODIMENT

Figure 1:
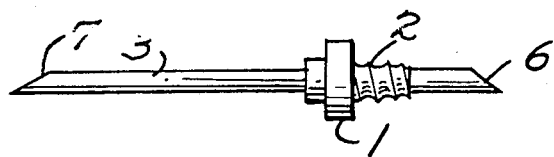
FIG. 1 is a side view of a double pointed syringe needle.
Figure 2:
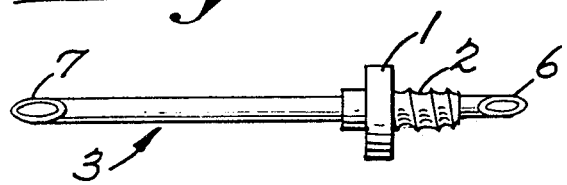
FIG. 2 is a top view of a double pointed syringe needle.

In the first exemplary embodiment, FIG. 1 shows a side view of a double pointed syringe needle including the needle shaft (3), the point (6) for entering the syringe, the point (7) for entering the patient's body, and attachment hub portion (2) and a collar portion (1). The hub portion (2) is adapted for attachment to the outlet end of a syringe, and includes a medial passageway containing a portion of the needle shaft (3) enabling tight securement of the needle to the syringe for liquid flow to or from the outlet of the syringe. The collar portion (1) is an integral part of the attachment hub (2) for positioning the hub (2) in relation to the syringe outlet. FIG. 2 shows a top view of the syringe needle shown in FIG. 1. Depending upon the syringe outlet to which the syringe needle assembly will be affixed, the hub portion (2) and collar portion (1) may be of a different structure. FIGS. 1 and 2 show an, exemplary collar portion (1) with a short axis in FIG. 1 and a long axis in FIG. 2.

Figure 5:
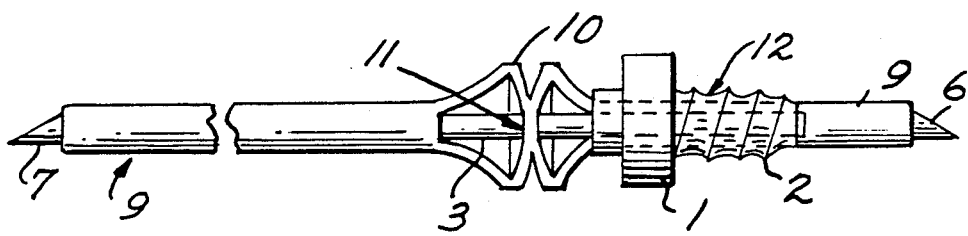
FIG. 5 is a side view of the first embodiment of the invention.

As shown in FIG. 5, the presently claimed syringe needle sheath is employed on the syringe needle shown in FIGS. 1 and 2. The sheath (9) surrounds the needle shaft (3) extending the length of the shaft, leaving both of the needle points (6 and 7) exposed. The sheath (9) includes at least two radially expanded portions of the sheath (10) which when compressed, forces both ends of the sheath (9) to slide in opposite directions along the shaft (3) to extend beyond and cover both points (6 and 7). In particular, FIG. 5 shows four radially expanded portions (10) of the sheath (9) being two pairs, each pair expanded in a direction opposite the other pair. Each radially expanded portion of each pair is joined together by a ring portion (11) which is attached to the needle shaft (3). The attached ring (11) provides a fixed point from which the sheath (9) extends in opposite directions along the shaft, towards and covering the points (6 and 7). That portion of the sheath (9) which extends toward point (6) passes through the medial passage way of hub (2) where the sheath may form extending arms (12) beneath the hub (2). Such extending arms (12) would reduce friction of the sheath against the shaft and inner wall of the medial passageway within the hub (2). The hub (2) is attached to the needle shaft (3).

Figure 6:
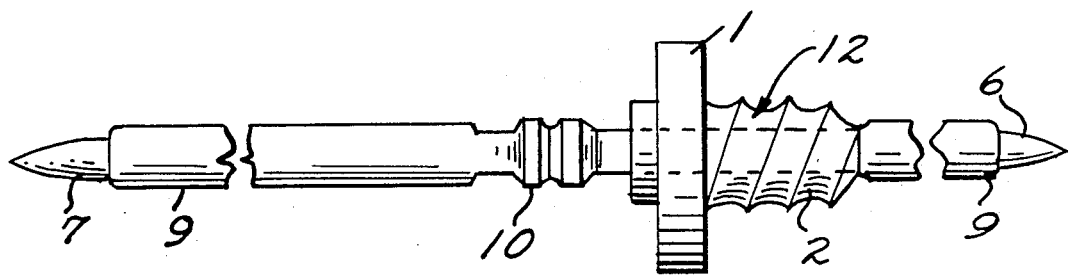
FIG. 6 is a top view of the first embodiment of the invention shown in FIG. 5.

FIG. 6 shows a top view of the syringe needle assembly of FIG. 5 and particularly shows the four radially expanded portions of the sheath to have a width approximately the same as the sheath (9). Further, the extension arms (12) may also have a width approximately the same as the sheath (9).

Figure 7:
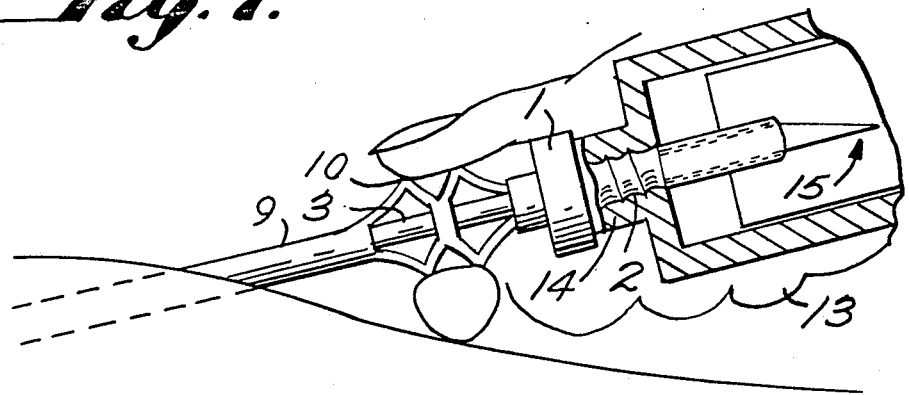
FIG. 7 shows the first embodiment of the invention shown in FIG. 5 being actuated by fingertip compression.

As shown in FIG. 7, the hub (2) enables tight securement of the needle to the syringe (15) by fitting within the syringe outlet (14). The collar (1) aids in positioning the hub (2) in relation to the syringe outlet (14). In particular, FIG. 7 shows the hand of a medical practitioner (13) grasping the present syringe needle sheath with fingertips, compressing radially expanded portions (10) which will force the sheath (9) to slide in opposite directions along the shaft (3) to extend beyond and cover both points (6 and 7).

Figure 8:
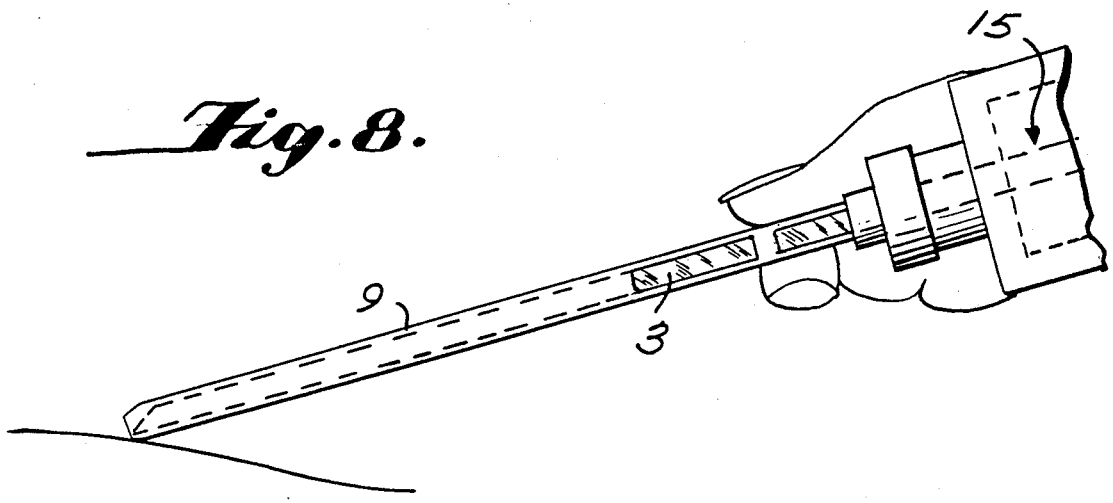
FIG. 8 shows the first embodiment of the invention shown in FIG. 7 after fingertip compression.

FIG. 8 shows the present syringe needle sheath of FIG. 7 having been completely compressed by fingertips to a completely extended state covering the end potions of shaft (3) and points (6 and 7). Thus, not only are the points (6 and 7) of the needle covered, but the end portions of the shaft (3) are also covered.

Figure 9:
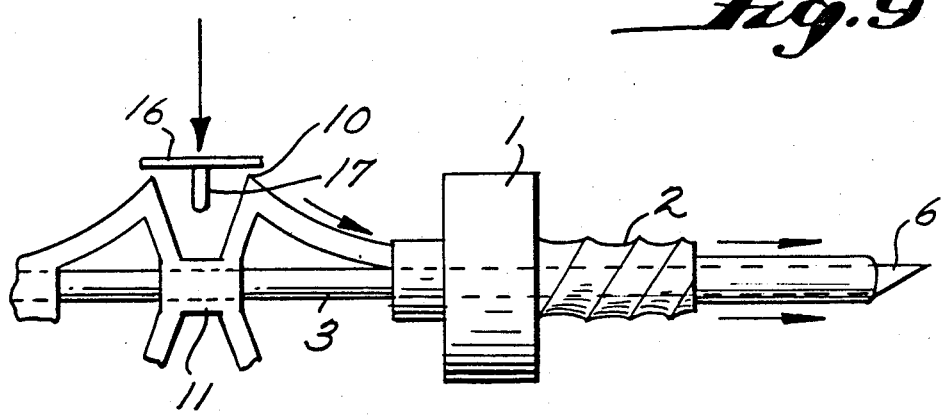
FIG. 9 is a partial side view of the syringe assembly, showing a compression platform with locking member.

As shown in FIG. 9, a compression platform (16) may be employed to press upon the outer area of the radially expanded portions (10), thus providing greater fingertip control. The compression platform (16) may include a locking member (17), for example, a resilient clamp, so that when compression platform (16) is compressed, the clamp is forced to open about the ring (11) or shaft (3), locking to it by friction. This will provide further securement of the extended sheath (9) to ensure non-retraction of the sheath (9).

In this first embodiment, the hub (12) and collar (1) are not necessary for function of the sheath (9) and hence may be of a radically different structure or even non-existent.

The apparatus of both the first, second and third embodiments may be formed of a readily moldable plastic, for example, polyurethane, or a combination of moldable plastic and metal portions. When the syringe assembly is to be reused then it must be formed of materials enabling it to be repeatedly subjected to sterilization temperatures. When the syringe assembly is to be disposed after a single use then the portions formed of plastic ma have a melting point above 150° C. to ensure non-reusability after being suscepted to such temperatures. Regardless of intended use, the materials of the present apparatus are biologically inert.

Figure 3:
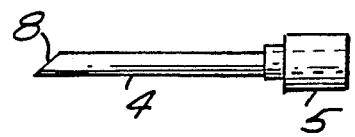
FIG. 3 is a side view of a single pointed syringe needle.
Figure 4:
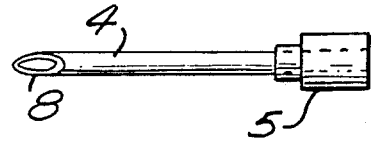
FIG. 4 is a top view of a single pointed syringe needle.
Figure 10:
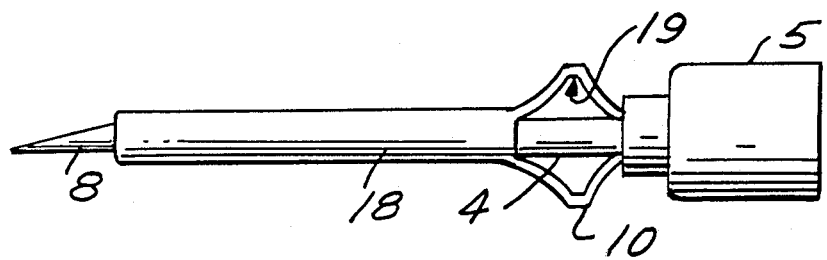
FIG. 10 is a side view of the second embodiment of the invention.

For the second exemplary embodiment, FIG. 3 shows a single pointed syringe needle having point (8), shaft (4) and attachment hub (5). The shaft (4) extends medially through the hub (5) with the flat end of shaft (4) generally flush with the edge of hub (5). The hub (5) enables tight securement of the needle to the syringe for liquid flow to or from the outlet of the syringe. FIG. 4 shows a top view of the single pointed syringe needle assembly in FIG. 3. As shown in FIG. 10, the syringe needle sheath (18) of the second exemplary embodiment for a single pointed syringe needle has at least one radially expanded portion (10) and in FIG. 10, has two radially expanded portions (10), expanded in opposite directions. The ends of the radially expanded portions (10) opposite point (8) are anchored to hub (5). Upon fingertip compression of radially expanded portions (10), sheath (18) is forced to slide in an axial direction along the shaft (4) towards point (8) so that sheath (18) extends beyond and covers point (8). While not shown, the second exemplary embodiment may also include a compression platform at the outer area of the radially expanded portion (10) to facilitate fingertip control. Further, at the inner vertex (19) of the radially expanded portion (10), a locking member may engage with shaft (4) upon compression of radially expanded portion (10).

Figure 11:
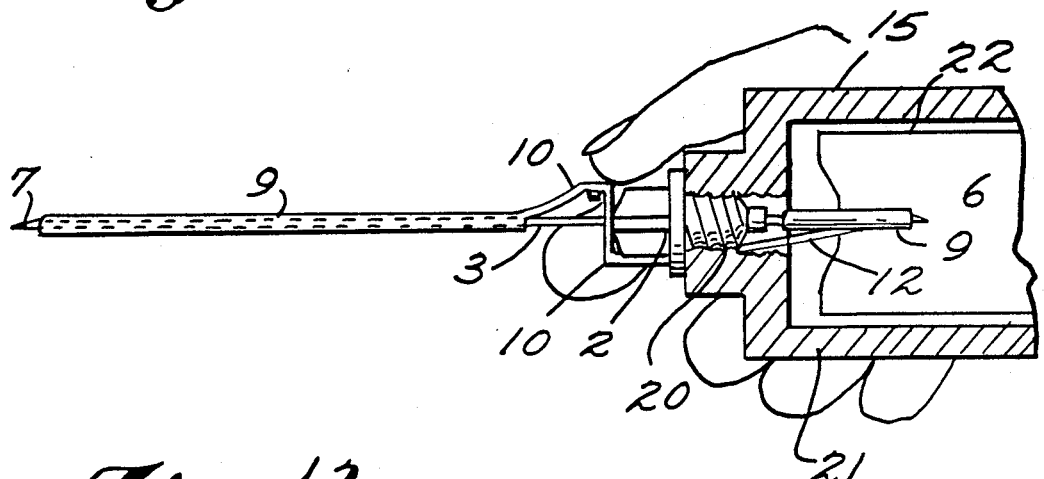
FIG. 11 is a side view of the third embodiment including the outlet of the syringe.
Figure 13:
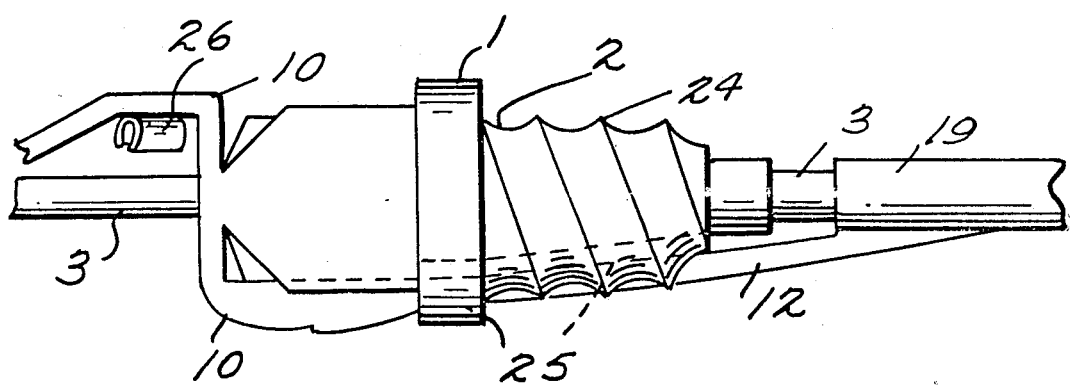
FIG. 13 is an enlargement of a portion of the third embodiment shown in FIG. 11.

For the third exemplary embodiment, FIG. 11 shows a double pointed syringe needle having needle shaft (3), the point (6) for entering the syringe, the point (7) for entering the patient's body, and attachment hub portion (2). Syringe (15) is shown with outlet (14) having interior threads (20) along its interior bore. Sheath (9) surrounds the needle shaft (3), substantially extending the length of the shaft except for the intermediate section where the hub (2) is located, leaving both of the needle points (6 and 7) exposed. Sheath (9) may, for example, and as shown, surround the shaft (3), in two segments. The two segments of the sheath (9) are connected by at least two radially expanded portions (10) which, when compressed, force both segments of the sheath to slide in opposite directions along the shaft (3) to extend beyond and cover both points (6 and 7). Sheath arm (12) extends from one of the radially expanded portions (10) over the exterior of hub (2) to connect with the segment of the sheath (9) for point (6), as best seen in FIGS. 13 and 11. The placement of sheath arm (12) differs from the first embodiment where the sheath arm is located medially to said hub (2). The hub (2) is initially attached to the needle shaft (3). Syringe (15) may have outlet (14) as part of an outer jacket (21) into which is slid, tube (22), as in, for example, a Vacutainer syringe.

Figure 12:
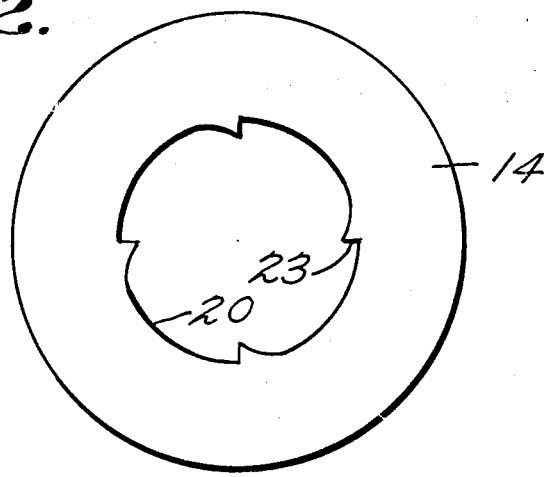
FIG. 12 is a side view of the syringe outlet in FIG. 11.

As shown in FIG. 12, syringe outlet (14) has an interior bore with threads (20) and a plurality of locking pawls (23) for operation in conjunction with the sheath arm (12) in a manner to be explained below.

FIG. 13 show hub (2) with exterior threads (24) on the posterior end of the hub (2), i.e., towards the syringe (15). As part of a hub locking mechanism, channel or groove (25) is formed in the longitudinal periphery of hub (2) so that sheath arm (12) rests in the outer portion of that channel (25). Channel (25) is of sufficient depth so that upon compression of radially expanded portion (10), the sheath arm (12) slides down and contacts the bottom of channel (25) so that the exterior surface of the sheath arm (12) is axially inward of the threads (24).

Locking device (26) is located on the inner surface of radially expanded portion (10) as shown in FIG. 13 and may be, for example, a friction clamp in the form of a tube having a slit facing the needle shaft (3) so that upon compression of radially expanded portion (10), the clamp (26) is forced down and open upon contacting the shaft (3), the walls of the tube spreading over and resiliently compressing about the shaft (3), thus securely locking the about shaft (3).

Figure 14:
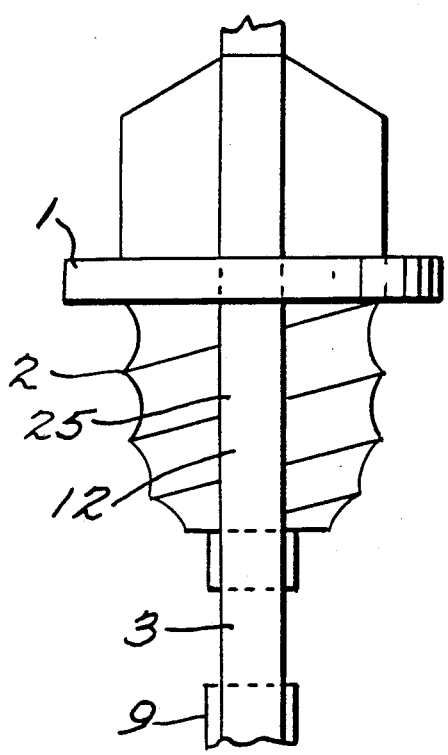
FIG. 14 is a bottom view of the third embodiment shown in FIG. 13.

FIG. 14 shows a bottom view of hub (2) having channel (25), and sheath arm (12) resting inside channel (25).

Figure 15:
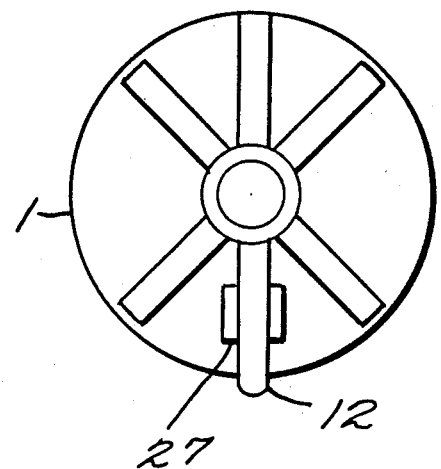
FIG. 15 is a side view of the third embodiment shown in FIG. 13.

FIG. 15 shows a side view of hub (2) with collar (1), in this case having an adit or bore (27) cut through collar (1 so that sheath arm (12) goes through the adit (27) as a tunnel rather than an open channel.

A medical practitioner, in employing the third embodiment of the present invention, would screw hub (2) into syringe outlet (14), whereby the outer surface of sheath arm (12) would, in screwing clockwise, glide up and over pawls (3) on the interior of syringe outlet (14). An attempt to unscrew hub (2) from syringe (15) would be unsuccessful because of sheath arm (12) striking the perpendicular face of pawls (23). After use of the syringe assembly, the medical practitioner would grasp the present syringe needle sheath with fingertips, compressing radially expanded portions (10) which forces the sheath (9) to slide in opposite directions along the shaft (3) to extend beyond and cover both points (6 and 7). Locking device (26) would irretractably engage upon needle shaft (3). Upon compression of radially expanded portions (10), sheath arm (12) is forced down into the bottom of channel (25) beneath or axially inward of threads (24) of hub (2). Thus, sheath arm (12) no longer engages pawls (23), and hub (2) may be safely unscrewed from syringe (12) because point (6) will be covered (as well as point (7)).

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

What is claimed is:

1. A syringe needle assembly including a double pointed needle comprising:

a needle having a shaft means with a point a each end thereof, one for entering the syringe and one for entering the patient; and a puncture-proof sheath means surrounding a major portion of the shaft means of said needle and normally extending substantially the entire length of said shaft means while leaving both of said needle points exposed, said sheath means including at least two radially expanded, inner portions joined together by a portion attached to said shaft, said radially expanded portions being axially compressible to force both outer ends of the sheath means to slide in opposite directions along said shaft means to extend beyond and nonretractably cover both points.

2. The structure according to claim 1, further including:

a hub portion adapted for attachment to the outlet end of the syringe, said hub including a medial passageway containing a portion of said needle shaft means, the hub being attached to said shaft means, said hub enabling tight securement of said needle to the syringe for liquid flow to or from the outlet of said syringe.

3. The structure according to claim 2, wherein said outlet of said syringe includes interior threads, said hub having complementary threads to engage the threads of said outlet.

4. The structure according to claim 3, wherein said syringe outlet and said hub form in combination a locking structure including:
   said syringe outlet having a plurality of rachet pawls on the interior of said outlet;
   said hub having a channel at the periphery and parallel to said shaft means;
   one of said radially expanded portions of said sheath means having an extending member at the exterior of and along the length of said hub channel, being resiliently compressible into said channel so that when compressed, the outer surface of said extension member is interior of the trough of said hub threads.

5. The structure according to claim 4, wherein said pawls are distributed on the interior of said syringe outlet in substantially one plane, perpendicular to the longitudinal axis of said syringe.

6. The structure according to claim 1, wherein said sheath means is formed of a readily moldable plastic.

7. The structure according to claim 1, wherein said sheath means may be subjected to sterilization temperatures enabling repeated use of said syringe assembly.

8. The structure according to claim 7, wherein said plastic is polyurethane.

9. The structure according to claim 7, wherein said plastic melts at temperatures above 150° C.

10. The structure according to claim 7, wherein said plastic is biologically inert.

11. The structure according to claim 1, wherein said radially expanded portion of said sheath may be compressed by the fingertips of one hand, forcing the sheath to cover the points.

12. The structure according to claim 1, wherein said radially expanded portions of said sheath means are approximately the same width as the sheath means surrounding said needle.

13. The structure according to claim 1, wherein there are two radially expanded portions, one portion expanded in a direction opposite the second portion.

14. The structure according to claim 1, wherein at least one of said radially expanded portions of said sheath means has a clamp-like locking device including, a tube attached to the inner side of said expanded portion, facing said shaft means, said tube being open ended and having an open slit along the length of said tube wall facing said shaft means, said tube being able to resiliently open along said slit and fit over a portion of said shaft means, resiliently and firmly locking to said shaft means.

15. A syringe needle assembly including a double pointed needle comprising:
   a needle having a shaft means with two points, one for entering the syringe and one for entering the patient; and
   a puncture-proof sheath means surrounding a major portion of the shaft means of said needle and normally extending substantially the entire length of said shaft means while leaving both of said needle points exposed, said sheath means including at least two radially expanded, inner portions joined together by a portion attached to said shaft means, said radially expanded portions being axially compressible to force both outer ends of the sheath means to slide in opposite directions along said shaft to extend beyond and non-retractably cover both points.

16. The structure according to claim 15, further including:
   a hub portion adapted for attachment to the outlet end of the syringe, said hub including a medial passageway containing a portion of said needle shaft means, the hub being attached to said shaft means, said hub enabling tight securement of said needle to said syringe for liquid flow to or from the outlet of said syringe.

17. The structure according to claim 15, wherein said sheath means is formed of a readily moldable plastic.

18. The structure according to claim 17, wherein said plastic is polyurethane.

19. The structure according to claim 17, wherein said plastic melts at temperatures above 150° C.

20. The structure according to claim 17, wherein said plastic is biologically inert.

21. The structure according to claim 15, wherein said sheath means may be subjected to sterilization temperatures enabling repeated use of said syringe assembly.

22. The structure according to claim 15, wherein said radially expanded portions of said sheath means may be compressed by the fingertips of one hand, forcing the sheath means to slide and cover both points.

23. The structure according to claim 15, wherein said radially expanded portions of said sheath are approximately the same width as the sheath means surrounding said needle.

24. The structure according to claim 15, wherein there are four radially expanded portions, one pair expanded in a direction opposite the second pair.

25. The structure according to claim 15, further including a compression platform fixed to a distal area of one or more of said radially expanded portions, facilitation application of fingertip pressure and control.

26. The structure according to claim 25, wherein said compression platform further includes one or more locking members attached to said platform, which upon pressing said platform, flattening said radially expanded portions, said locking member engages at least one of said needle shaft and sheath.

27. A syringe needle assembly including a single pointed needle comprising:
   a needle having a shaft means with one point and one flat end, the flat end for interfacing with the outlet of said syringe and the pointed end for entering the patient;
   a hub portion adapted for attachment to the outlet end of the syringe, said hub including a medial passageway containing a portion of said needle shaft means, the hub being attached to said shaft means, said hub enabling tight securement of said needle to said syringe for liquid flow to or from the outlet of said syringe; and
   a puncture-proof sheath means surrounding the shaft means of said needle and normally extending substantially the entire length of said shaft means, one end of said sheath means being securely fixed to said attachment hub, the pointed end of said needle being exposed, said sheath means including two radially expanded inner portions of the sheath means, one portion expanded in a directional opposite the second portion, which when both are compressed, forces the unfixed end of said sheath means to slide a direction along said shaft to extend beyond and non-retractably cover said point.

28. The structure according to claim 27, wherein said compression platform further includes one or more locking members attached to said platform, which upon pressing said platform, flattening said radially expanded portion, said locking member engages said needle shaft.

29. A syringe needle assembly including a single pointed needle comprising:
   a needle having a shaft means with one point and one flat end, the flat end for interfacing with the outlet of said syringe and the pointed end for entering the patient;
   a hub portion adapted for attachment to the outlet end of the syringe, said hub including a medial passageway containing a portion of said needle shaft means, the hub being attached to said shaft means, said hub enabling tight securement of said needle to said syringe for liquid flow to or from the outlet of said syringe;
   a puncture-proof sheath means surrounding the shaft means of said needle and normally extending substantially the entire length of said shaft means, one end of said sheath means being securely fixed to said attachment hub, the pointed end of said needle being exposed, said sheath means including at least one radially expanded inner portion of the sheath means which when compressed, forces the unfixed end of said sheath means to slide in a direction along said shaft to extend beyond and nonretractably cover said point; and
   a compression platform fixed to a distal area of one or more of said radially expanded portions, facilitating application of fingertip pressure and control.

* * * * *